United States Patent
Rutenberg et al.

(10) Patent No.: US 9,068,975 B1
(45) Date of Patent: Jun. 30, 2015

(54) COMPUTERIZED DETECTION OF LARYNGOPHARYNGEAL REFLUX

(71) Applicant: CDx Diagnostics, Inc., Suffern, NY (US)

(72) Inventors: Mark Rutenberg, Monsey, NY (US); Stephen Frist, Maleh Adumim (IL)

(73) Assignee: CDx Laboratories, Inc., Suffern, NY (US)

( * ) Notice: Subject to any disclaimer, the term of this patent is extended or adjusted under 35 U.S.C. 154(b) by 0 days.

(21) Appl. No.: 13/960,763

(22) Filed: Aug. 6, 2013

Related U.S. Application Data

(63) Continuation-in-part of application No. 12/817,963, filed on Jun. 17, 2010, now Pat. No. 8,501,425.

(51) Int. Cl.
*G01N 33/48* (2006.01)
*G01N 33/50* (2006.01)

(52) U.S. Cl.
CPC .................................. *G01N 33/5091* (2013.01)

(58) Field of Classification Search
CPC .................................................... G01N 33/5091
See application file for complete search history.

*Primary Examiner* — James Martinell
(74) *Attorney, Agent, or Firm* — Levisohn Berger LLP

(57) ABSTRACT

A method and apparatus for determining a likelihood of LPR by analyzing a laryngeal cell preparation. The laryngeal sample is fixed on a microscope slide and analyzed by a microscope combined with an image acquisition system and a computer having an image recognition system. The image recognition system detects mobile cells that are implicated in the body's inflammatory response and counts how many of such cells are on the slide. The computer generates an absolute number of such cells and percentage values for such cells out the total number of mobile cells classified. The computer then utilizes the absolute numbers, the ratios of mobile cells with respect to each other—or a combination of both to generate a score. The score represents a probabilistic determination of inflammation.

9 Claims, 3 Drawing Sheets

COMPUTERIZED DETECTION OF LARYNGOPHARYNGEAL REFLUX

RELATED APPLICATIONS

This application is a Continuation-In-Part of U.S. patent application Ser. No. 12/817,963, filed Jun. 17, 2010 and which is to issue as U.S. Pat. No. 8,501,425 on Aug. 6, 2013—the contents of which are incorporated by reference herein.

FIELD OF THE INVENTION

The invention relates to the field of computer-assisted diagnosis of cytological preparations, more specifically to a method and apparatus for determining a likelihood of Laryngopharyngeal Reflux (LPR).

BACKGROUND OF THE INVENTION

Laryngopharyngeal Reflux (LPR) is a medical condition in which acid that has backflowed from the stomach traverses into the esophagus and continues into the throat. Typically, this is due to a sphincter that is not functioning properly in blocking such backflow.

Both patient and physician are faced with numerous difficulties in attempting to diagnose LPR. Current diagnostic approaches, such as 24 hour pH testing are both intrusive and uncomfortable. This problem is compounded by the fact that the symptoms consistent with LPR are identical to those of various other upper respiratory conditions. As such, a physician is necessarily faced with the dilemma of whether or not to undertake such invasive measures as pH testing when in fact the source of the patient's symptoms may be attributed to a wide-ranging array of conditions. Moreover, it is difficult to monitor a patient over time using current techniques.

SUMMARY OF THE INVENTION

The current invention solves these problems with a minimally invasive in-office brush biopsy procedure during which a cell sample of a patient's laryngeal tissue is collected. The specimen is then imaged by a computer and a quantitative analysis is performed by a specialized computer to detect cell populations and cell type ratios that may be indicative or consistent with LPR.

A specialized sampling brush threaded through the operative channel of an endoscope is used to collect a cell sample of the larynx and/or pharynx. During this procedure a specially designed brush biopsy instrument is threaded down the channel of an endoscope, Biopsy instrument U.S. Pat. Nos. 6,494,845, 6,676,609 and 7,004,913 are incorporated herein by reference. The brush obtains a transepithelial specimen of the laryngeal or pharyngeal tissue, which is analyzed by a specially trained neural network computer. Computerized system U.S. Pat. Nos. 6,297,044 and 6,284,482 are incorporated by reference.

A determination of a likelihood of LPR will be determined by examining a brush biopsy of the posterior aspect of the larynx, the interarytenoid mucosa, for characteristic quantitative cellular changes and disease specific molecular markers. The cellular sample is analyzed by a computer having a specially trained image recognition system to detect the presence of at least two important white blood cell types, namely: polymorphonuclear leukocytes (PMN's) and lymphocytes. The system then counts the number of each of these cell types in the sample vis-à-vis the total number of white blood cells on the slide to determine a percentage value for each of the cell types. Using the percentage values for at least two of the white blood cell types, a probabilistic determination of the presence of pulmonary inflammation is generated.

In preferred embodiment of the invention, a probabilistic determination of the presence of LPR is made through a two dimensional analysis wherein a percentage value for at least two cells types are plotted as the x and y axis of a graph with the z axis representing the probability of the condition. The percentage values (or absolute values) of cells of interest are compared to expected percentage values (or absolute values). When percentage values (or absolute values) of two factors associated with LPR are detected are at increased levels—as compared to their respective expected values—a determination of a likelihood of LPR is generated.

Most preferably, the computer calculates a probability score based on the combined x and y values described above. The probability score represents a data point on a continuum. The score value increases when high percentages of white blood cells are detected and vice versa.

In a broad sense, the invention is a method of determining a presence of LPR, comprising the steps of examining a laryngeal cellular sample with a microscope combined with an image acquisition system; acquiring images of cells in the cellular sample; analyzing the images of the cells with an image recognition system to detect at least two types of white blood cells; counting individual cells of each of the at least two types of white blood cells; generating at least two sums from the counts, each of the sums representing a number of individual cells; comparing each sum of at least two cell types to an average number of expected cells for each of the cell types and/or comparing the percentages of each cell type to an expected percentage of each cell type; and generating a score based on the comparison, where the score is a probabilistic determination of a likelihood of inflammation.

DETAILED DESCRIPTION OF THE INVENTION

Figure 1:
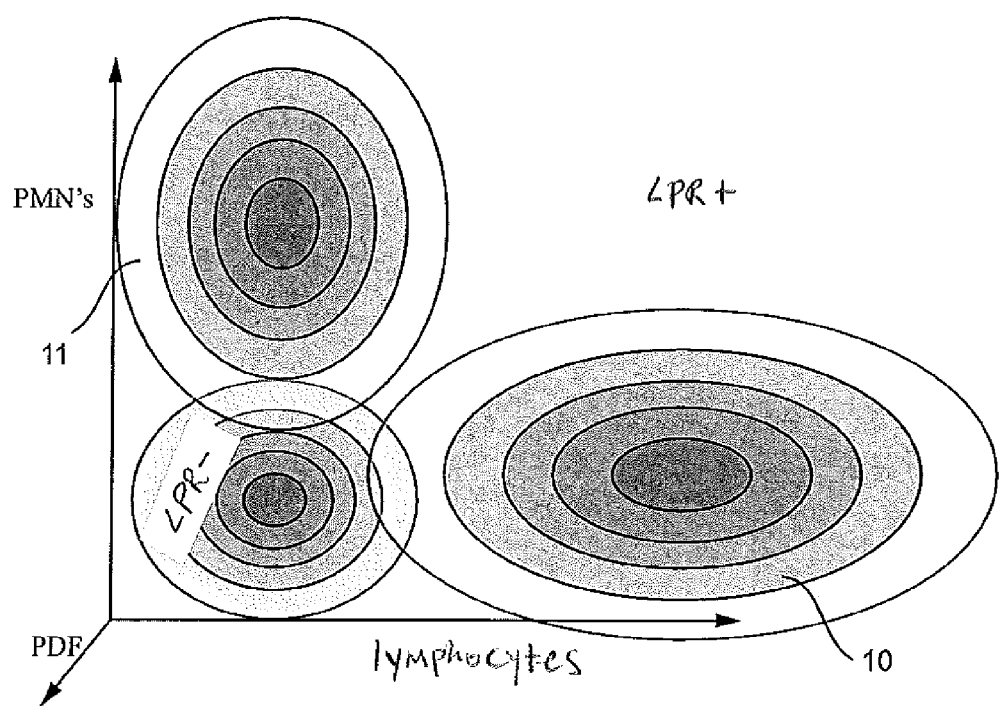
FIG. 1 is a schematic representation of a three-dimensional analysis for acute inflammation consistent with LPR according to an embodiment of the invention.

Embodiments of the present invention will now be described with reference to the above-identified figures of the Drawings. However, the Drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

Inflammation occurs as part of a tissue's local response to pathogen invasion, injury or other irritation. The immune response to such injurious conditions is characterized by, both, physiological and cellular/molecular defensive processes of recognizing and destroying invasion or injury.

In the physiological process, blood vessels in the affected region become dilated and capillary permeability becomes increased. This inflammatory response allows for increased blood flow to an affected region and for specialized hematopoietic and mobile tissue cells to be quickly and abundantly dispatched to their site of action ("mobile cells" herein refers to non-structural cells).

The cellular response includes the recruitment of various specialized cells of the body's immune system to destroy or otherwise neutralize an offending or injurious agent.

There are generally two stages associated with inflammation—namely "acute" and "chronic" stages. The early stage is termed the acute stage and is the body's initial response to a tissue irritation. If such irritation persists, the immune response enters into the chronic stage. There are specialized white blood cells that tend to be at elevated levels in the acute stage and different ones that tend to exist at elevated levels in the chronic stage.

When gastric cells migrate to the larynx in patients suffering from GERD or reflux, the body's immune system initiates an inflammatory response.

The laryngeal epithelium consists of three predominant cell types: ciliated, secretory (mucin producing), and stratified squamous epithelial cells. The epithelial cells form a tissue and architecturally there is basal to surface maturation, intercellular spaces and intercellular junctional complexes. Thus, cellular sample obtained from the larynx will contain these structural cells.

In addition, laryngeal sample will contain a number of hematopoietic cells. However, when hematopoietic cells are found at increased levels—it may indicate a presence of LPR.

The cells noted in the mucosa that are of interest for a diagnosis of LPR include various leukocytes that are found to be elevated in the acute and chronic stages of inflammation, respectively. Acute inflammation is characterized primarily by polymorphonuclear leukocytes (PMNs) and lymphocytes. The other source of reactive cells is macrophages in variable numbers.

The chronic inflammation noted in a more prolonged gastric reflux challenge is characterized primarily by lymphocytes and PMNs. Noted in smaller numbers will be other hematopoietic cells—plasma cells, eosinophils and mast cells as well as macrophages.

In the inventive system a laryngeal cellular sample is fixed and prepared on a slide in a manner known to one of skill in the art. However, instead of manually examining the slide, it is analyzed by a computer having specialized hardware and software to carry out the analysis of the invention.

In a preferred embodiment, a microscope combined with an image capture device incrementally moves across the slide capturing images of the slide at each increment. An image recognition system analyzing the captured images is trained to classify the cells of interest on a cell-by-cell basis and count how many cells of cell-types of interest are present.

The inventive system will first classify the various structural and inflammatory cells found on the slide and count the absolute numbers of each—to yield a sum of each cell of interest on the slide. The system will then calculate the absolute number of all white blood cells combined. Thereafter, the system will determine the percentage of specific white blood cells with respect to the total number of white blood cells found in the specimen. Similarly, the system will calculate the absolute number of all epithelial cells combined. Thereafter, the system will determine the percentage of specific epithelial cell types with respect to the total number of epithelial cells.

A specimen that is found to have about 90% or more PMNs and about 10% lymphocytes—will be deemed to be indicative of the acute phase of LPR. Inversely, a specimen found to have about 90% or more lymphocytes and about 10% PMNs will be deemed to be indicative of the chronic phase of LPR. It will be understood that different ranges may be used in different embodiments of the invention. Preferably, a determination of acute LPR is made when PMNs are present at ratios between 75%-99% of total white blood cells and lymphocytes are present at rations between 1% and 10% of total white blood cells. Inversely, a determination of chronic LPR is made when lymphocytes are present at ratios between 75%-99% of total white blood cells and PMNs are present at rations between 1% and 10% of total white blood cells.

In addition to the percentages of white blood cells extrapolated by the cell counts—the absolute number of cells may be utilized to generate a probability of inflammation. That is, based on data obtained from normal patients, an average number of white blood cells are determined. If the absolute number of at least two white blood cells of interest are higher than average—a probability of inflammation would be indicated. As the spread of cells above average increases, a score value correspondingly increases.

In an embodiment of the invention, the percentage measure and absolute number metric are combined. Specifically, if absolute cells numbers are found to be above a threshold number and the percentages of cells are within certain ratios—a probability of inflammation is determined.

In the case of long term insult, there will be thickening of the laryngeal mucosa with an increase in superficial epithelial cells noted histologically and a concomitant increase in superficial cells in the brush biopsy specimen. The percentage of superficial epithelial cells signifying this change will be more than 95% of the total epithelial cell count. That is, the computer counts the total number of epithelial cells present in a laryngeal cellular sample. If superficial epithelial cells account for about 95% of the epithelial cells—then such finding is considered as a factor indicating a possibility of chronic LPR. The computer then calculates the percentage values of the white blood cells on the slide. If lymphocytes are found to represent of 75-99% of the total white blood cells, then the two factors combined (namely, increased percentage of superficial epithelial cells and increased percentage of lymphocytes) indicate a likelihood of chronic LPR. In a preferred embodiment of the invention, an increased level of superficial epithelial cells is considered as a factor in diagnosing chronic LPR when such superficial epithelial cells are found to represent anywhere between 85%-99% of the epithelial cells in a cellular specimen. Most preferably, the range is between 85% and 95%.

Another change in the mucosa that is frequently noted is ulceration. In this case, if the brush is limited to the ulcerated area, the superficial epithelial cells will be diminished and the relative and absolute number of basal cell will be increased. The percentage of basal cells signifying this change will be more than 90% of the total epithelial cell count. That is, the computer counts the total number of epithelial cells present in a laryngeal cellular sample. If basal cells account for about 90% of the epithelial cells—then such finding is considered as a factor indicating a possibility of chronic LPR. The computer then calculates the percentage values of the white blood cells on the slide. If lymphocytes are found to represent of 75-99% of the total white blood cells, then the two factors combined (namely, increased percentage of basal cells and increased percentage of lymphocytes) indicate a likelihood of chronic LPR. In a preferred embodiment of the invention, an increased level of basal cells is considered as a factor in diagnosing chronic LPR when such basal cells are found to represent anywhere between 80%-90% of the epithelial cells in a cellular specimen. (Note, "increased levels" herein refer to percentages or absolute numbers of cells that are above an expected percentage value or absolute value.)

Below are some examples of specific embodiments of the invention for determining each of acute and chronic LPR. In all embodiments mentioned below, the computer searches for PMNs, macrophages, lymphocytes, eosinophils, plasma cells and mast cells.

Acute LPR

Example 1

A larynegeal sample is analyzed for a presence of PMNs, marcrophages, lymphocytes plasma cells and mast cells. If PMNs are found to account for about 75-99% percent of such white blood cells and lymphocytes account for about 1-10% of such cells—a probability of acute LPR is determined.

Alternatively, if the absolute number of PMNs is from 50,000-500,000 cells and the absolute number of lymphocytes is from 10,000-100,000 cells, a probability of acute LPR is determined.

In one preferred embodiment, both the absolute numbers and percentages are plotted, whereby if both the percentages and the absolute numbers of PMNs and lymphocytes are within the above-cited ranges, a probability of acute pulmonary inflammation is determined.

FIG. 1, schematically shows a three-dimensional analysis of the invention. A high number of lymphocytes 10, may in itself indicate inflammation. However, it also is possible that there is no inflammation. Similarly, an elevated number of PMNs 11, may or may not be as a result of inflammation. However, when these two parameters are combined, patients that are positive for inflammation are distinguished from those that are negative—with a high degree of accuracy. That is, either increased absolute numbers of PMNs or lymphocytes, or increased percentages of these cells with respect to each other or with respect to other white blood cells—or some combination of the two metrics—will allow for discrimination between patients that are negative and those that are positive for inflammation consistent with LPR.

Chronic LPR

Example 2

A larynegeal sample is analyzed for a presence of PMNs, marcrophages, lymphocytes plasma cells and mast cells. If PMNs are found to account for about 1-10% of such white blood cells and lymphocytes account for about 75-99% of such cells—a probability of chronic LPR is determined.

Alternatively, if the absolute number of lymphocytes is from 50,000-500,000 cells and the absolute number of PMNs is from 10,000-100,000 cells, a probability of chronic LPR is determined.

In one preferred embodiment, both the absolute numbers and percentages are plotted, whereby if both the percentages and the absolute numbers of lymphocytes and PMNs are within the above-cited ranges, a probability of LPR is determined.

FIG. 1, schematically shows a three-dimensional analysis of the invention. A high number of lymphocytes 10, may in itself indicate inflammation. However, it also is possible that there is no inflammation. Similarly, an elevated number of PMNs 11 may or may not be as a result of inflammation. However, when these two parameters are combined, patients that are positive for inflammation are distinguished from those that are negative—with a high degree of accuracy. That is, either increased absolute numbers of lymphocytes and PMNs, or increased percentages of these cells with respect to each other or with respect to other mobile cells—or some combination of the two metrics—will allow for discrimination between patients that are negative and those that are positive for inflammation.

Example 3

A larynegeal sample is analyzed for a presence of PMNs, marcrophages, lymphocytes plasma cells, mast cells and epithelial cells (including basal, intermediate and superficial epithelial cells). If superficial epithelial cells account for between 85%-95% of the total epithelial cells and lymphocytes account for about 75-99% of white blood cells—a probability of chronic LPR is determined.

Example 4

A larynegeal sample is analyzed for a presence of PMNs, marcrophages, lymphocytes plasma cells, mast cells and epithelial cells (including basal, intermediate and superficial epithelial cells). If basal cells account for between 80%-90% of the total epithelial cells and lymphocytes account for about 75-99% of white blood cells—a probability of chronic LPR is determined.

Figure 2:
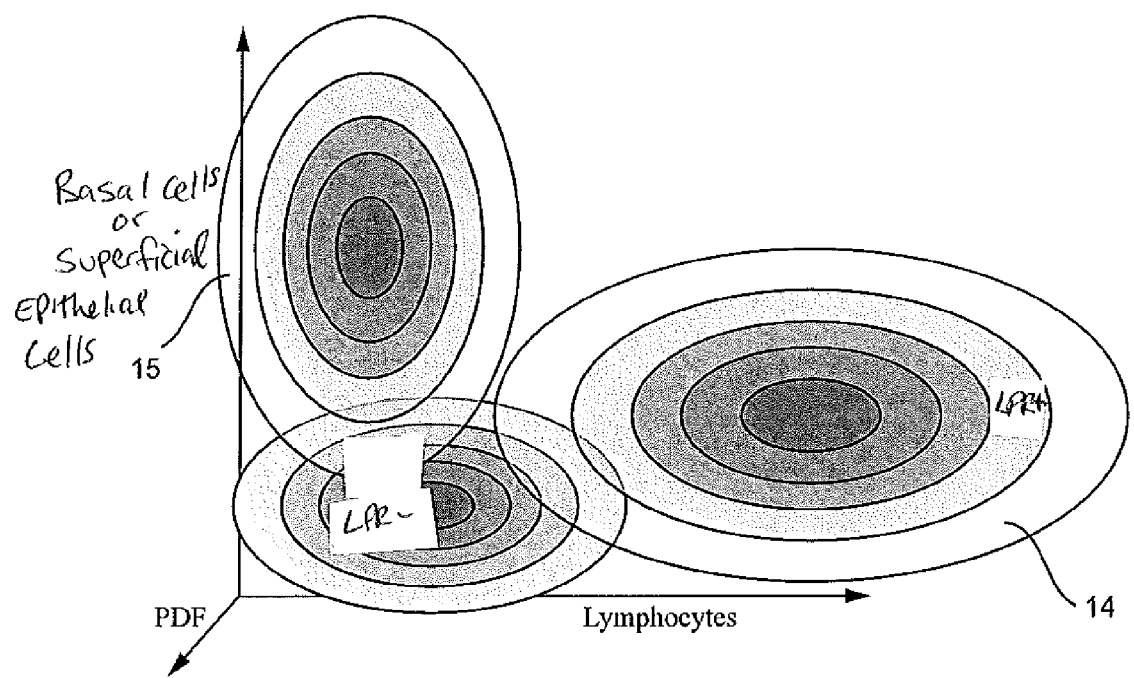
FIG. 2 is a schematic representation of a three-dimensional analysis for chronic inflammation consistent with LPR according to an embodiment of the invention.

FIG. 2, schematically shows a three-dimensional analysis of the invention. A high number of lymphocytes 14, may in itself indicate inflammation. However, it also is possible that there is no inflammation. Similarly, an elevated number of superficial epithelial cells or basal cells 15 may or may not be as a result of inflammation. However, when these two parameters are combined, patients that are positive for inflammation are distinguished from those that are negative—with a high degree of accuracy. That is, either increased absolute numbers of lymphocytes and superficial cells, or increased percentages of these cells with respect to each other or with respect to other mobile cells/epithelial cells—or some combination of the two metrics—will allow for discrimination between patients that are negative and those that are positive for inflammation. Alternatively, increased absolute numbers of lymphocytes and basal cells, or increased percentages of these cells with respect to each other or with respect to other mobile cells/epithelial cells—or some combination of the two metrics—will allow for discrimination between patients that are negative and those that are positive for inflammation.

In one preferred embodiment, both the absolute numbers and percentages are plotted, whereby if both the percentages and the absolute numbers of lymphocytes, PMNs, superficial epithelial cells and basal cells are within the above-cited ranges, a probability of acute or chronic inflammation associated with LPR is determined.

Figure 3:
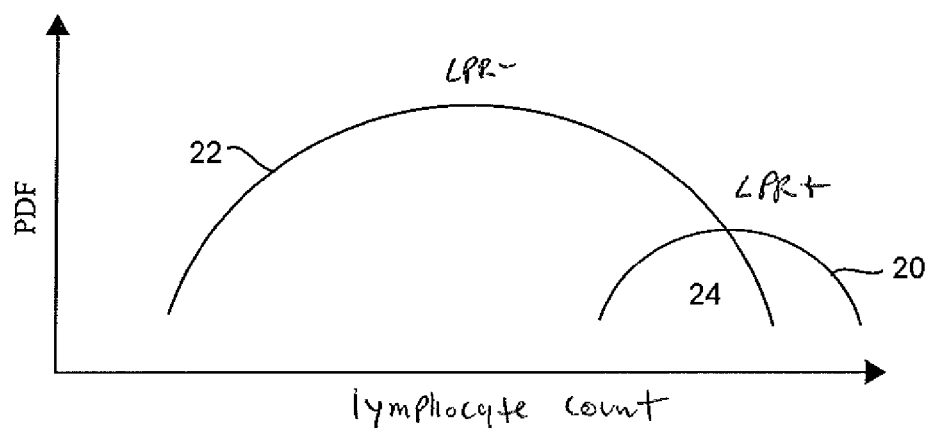
FIG. 3 is a schematic representation showing the shortcomings of two-dimensional analysis and the improvement of the analysis described herein.

In a preferred embodiment, in order to yield a probability of inflammation, a minimum of two parameters are examined. For example, to determine a probability of acute chronic inflammation, the system will determine whether or not each of PMNs and lymphocytes are present at elevated levels. This is referred to as a three-dimensional analysis. Analysis of a single parameter (cell-type) may lead to over-calling inflammation. For example, referring to FIG. 3, which shows a plot of lymphocytes, Arc 20 shows a level of lymphocytes that may be associated with inflammation. Arc 22 shows a range of lymphocytes within which a patient may be negative for inflammation. In the area of overlap 24, a patient may be called positive for inflammation when, in fact, he/she is negative for the condition. The same is true for PMNs (although not shown). However, when the two parameters are combined (as shown in FIG. 1) patients with inflammation are separated from those that are negative.

One of ordinary skill in the art would know how to train an image recognition system to classify epithelial cells and white blood cells based on well-known morphological characteristics. However, by way of example, the following are some morphological characteristics that may be examined. PMNs have nuclei are characterized by multi-lobed nuclei (usually 3-5 lobes—sort of blobs) held together by intervening "strings." With macrophages—the intracytoplasmic material has an appearance of "specks" in the cytoplasm (in contrast to their not being any in the nucleus). Lymphocytes may be observed as having a relatively smaller cytoplasmic volume (in two dimensions). An important feature for recognition of plasma cells is the area of cytoplasmic clearing (halo) adjacent to one side (the internal surface) of its nucleus.

It will be understood that the probability of inflammation can be a score, which represents a data point on a continuum. That is as the percentages of white blood cells of interest, epithelial cells of interest and/or the absolute numbers of cells increase—the score will correspondingly increase.

One possible way of displaying results of the computer analysis, is by way of histograms. For example, in an embodiment, histograms are presented having designated bins for each cell type. For instance, after classifying and quantifying cells a histogram having two distinct bins for lymphocytes, and PMNs is generated. The presence of these two cell types may indicate a presence of acute or chronic inflammation associated with LPR. To further approximate whether such condition exists, each bin is examined to determine a percentage value for each white blood type of the total number of white blood cells. If the ratios are found to be in the ranges described above, the slide will be deemed as "probable" for inflammation.

In a preferred embodiment, cell types are presented on the histogram only if a threshold number of that particular cell type is reached. For example, for PMNs a threshold may be set to 50,000. If less than 50,000 PMNs are detected—then PMNs are not included in the histogram.

It will be understood that the cell classification and cell counting may be performed in real time—or at a time after the images are acquired. That is, as the image acquisition system acquires images of cells, various cell parameters are examined to determine cell type. Once a cell type is determined (assuming that it is a cell of interest), it is added to a running tally in temporary storage on a computer. Once images corresponding to the entire or majority of a slide is acquired, it is stored as a digital image on a digital storage medium. Tallies of cells of interest also are stored on a storage medium—such as a computer hard drive.

Alternatively, as a first step, a slide is digitized and stored on a storage device. Thereafter, a computer, using an image recognition system analyzes the digitally stored images of cells to classify and quantify them according to the teachings of the invention.

Having described this invention with regard to specific embodiments, it is to be understood that the description is not meant as a limitation since further modifications and variations may be apparent or may suggest themselves to those skilled in the art. It is intended that the present application cover all such modifications and variation as fall within the scope of the appended claims.

What is claimed is:

1. A method of determining a presence of laryngopharyngeal reflux, comprising the steps of:
examining a slide comprising a laryngeal cellular sample with a microscope combined with an image acquisition system;
acquiring images of cells in said laryngeal cellular sample;
analyzing said images of said cells with an image recognition system to detect at least two types of mobile cells;
counting individual cells of each of said at least two types of mobile cells;
generating at least two sums from said counts, each of said sums representing a number of individual cells;
comparing each of said sums to an average number of expected cells for each of said cell types; and
generating a score based on said comparison, said score indicating a likelihood of inflammation.

2. The method of claim 1, wherein said at least two types of mobile cells comprise PMNs and lymphocytes.

3. The method of claim 1, further comprising the step of adding the sums from said counts to generate a sum of combined mobile cells and determining a percentage value for each cell type, said percentage value representing a percentage of a mobile cell type out of a sum of combined mobile cells.

4. The method of claim 3, wherein percentage values for at least two cell types and sums of individual cell numbers of said at least two cell types are combined to generate said score.

5. A method of determining a presence of laryngopharyngeal reflux, comprising the steps of:
examining a slide comprising a laryngeal cellular sample with a microscope combined with an image acquisition system;
acquiring images of cells in said laryngeal cellular sample;
analyzing said images of said cells with an image recognition system to detect at least first mobile cell type and a second mobile cell type;
counting individual cells of each of said first mobile cell type and said second mobile cell type;
calculating a total number of mobile cells on said slide;
generating a first percentage value, said first percentage value corresponding to a percentage of said first mobile cell type out of said total number of mobile cells;
generating a second percentage value, said second percentage value corresponding to a percentage of said second mobile cell type out of said total number of mobile cells;
comparing said first percentage value to a first expected value and comparing said second percentage value to said to a second expected percentage value; and
generating a score based on said comparisons, said score indicating a likelihood of inflammation.

6. The method of claim 5, whereby said mobile cells first mobile cell type comprises lymphocytes and said second cell type comprises PMNs.

7. A method of determining a presence of laryngopharyngeal reflux, comprising the steps of:
examining a slide comprising a laryngeal cellular sample with a microscope combined with an image acquisition system;
acquiring images of cells in said laryngeal cellular sample;
analyzing said images of said cells with an image recognition system to detect at least a first mobile cell type and a second mobile cell type;
analyzing said images of said cells with an image recognition system to detect at least two epithelial cell types;
counting individual cells of said first mobile cell type and said second mobile cell type;
counting individual cells of said first epithelial cell type and said second epithelial cell type cell type;

calculating a total number of mobile cells on said slide;

calculating a total number of epithelial cells on said slide;

generating a first percentage value, said first percentage value corresponding to a percentage of said first mobile cell type out of said total number of mobile cells;

generating a second percentage value, said second percentage value corresponding to a percentage of said first epithelial cell type out of said total number of epithelial cells;

comparing said first percentage value to a first expected value and comparing said second percentage value to said to a second expected percentage value; and generating a score based on said comparisons, said score indicating a likelihood of inflammation.

8. The method of claim 7, whereby said first mobile cell type is lymphocytes and said first epithelial cell type is superficial epithelial cells.

9. The method of claim 8, whereby said first mobile cell type is lymphocytes and said first epithelial cell type is basal cells.

\* \* \* \* \*